(12) United States Patent
Lewis

(10) Patent No.: US 6,279,408 B1
(45) Date of Patent: Aug. 28, 2001

(54) SAMPLE BAG

(75) Inventor: Gary W. Lewis, Foothill Ranch, CA (US)

(73) Assignee: Horiba Instruments, Inc., Irving, CA (US)

( * ) Notice: Subject to any disclaimer, the term of this patent is extended or adjusted under 35 U.S.C. 154(b) by 0 days.

(21) Appl. No.: 09/672,242

(22) Filed: Sep. 28, 2000

(51) Int. Cl.[7] ....................................................... G01N 1/14
(52) U.S. Cl. ....................................................... 73/864.62
(58) Field of Search ............................ 73/863.02, 863.03, 73/864.51, 864.62; 383/109, 113, 3, 116

(56) References Cited

U.S. PATENT DOCUMENTS

| | | | |
|---|---|---|---|
| 3,793,887 | * | 2/1974 | Anderson et al. ................. 73/863.03 |
| 5,074,155 | * | 12/1991 | Vecere .............................. 73/864.62 |
| 5,547,761 | * | 8/1996 | Chapman, Jr. et al. . |
| 5,756,199 | * | 5/1998 | Kerbow et al. . |
| 5,789,466 | * | 8/1998 | Birmingham, Jr. et al. . |
| 5,897,535 | * | 4/1999 | Feliziani et al. . |

OTHER PUBLICATIONS

Du Pont, Chemically Modified Free–Flow Granular Molding Resins—Teflon PTFE TE–6462 fluoropolymer resin, No date.

Proven Properties, New Grades: Dynenon™ PTFE and Dyneon™ TFM™ PTFE, pp. 2–5, No date.

* cited by examiner

Primary Examiner—Robert Raevis
(74) Attorney, Agent, or Firm—Brooks & Kushman P.C.

(57) ABSTRACT

A sample bag for collecting a mixture of gasses for analysis is made of a modified polymer consisting essentially of tetrafluoroethylene (TFE) and at most about 2.0 percent perfluoropropylvinylether (PPVE).

7 Claims, 2 Drawing Sheets

SAMPLE BAG

TECHNICAL FIELD

The present invention relates to a sample bag for collecting a mixture of gasses for analysis, and to a method of collecting a diluted exhaust gas mixture from an internal combustion engine.

BACKGROUND ART

A gas diluting and testing apparatus is used to analyze, among other things, vehicular exhaust. The apparatus uses a mixing system to dilute the exhaust gasses so that the moisture content of the gasses is sufficiently reduced in order to minimize errors due to condensation. One example of an existing mixing system is the constant volume sampler (CVS).

The CVS has been used for over twenty-five years to sample the emissions from automobiles. It is the device used for automotive emissions tests that are the basis for the certification that vehicles sold in the United States are compliant with the Clean Air Act.

Automotive sampling systems, as well as other analytical systems, utilize sealed bags for collecting engine exhaust gasses for analysis of components after the collection interval has been completed. In order to preserve the integrity of the captured sample, the sample bag material must be inert, non-reactive, without leaks, and must have low permeation for the specific gasses contained both within the bag and outside the bag. The sample bag must not emit or absorb gasses, and the bag material must be flexible for fill and empty cycling. In the past, materials used for construction of the sample bag walls have failed to meet one or more of the above criteria, and it is desirable to provide a sample bag that limits these various undesirable characteristics. As vehicles become cleaner, their emissions become more difficult to measure accurately. To overcome some of the inherent limitations of the CVS, some attempts have been made to develop improved mixing systems. In addition to the effects of the mixing system itself, mixing systems that collect a gas mixture with a sample bag may sometimes be limited in accuracy due to limitations of the sample bag.

Although many existing mixing systems and existing sample bags have been used in applications that are commercially successful, with increasing demands for more accurate measurement techniques, it is desirable to make improvements to existing measurement and dilution techniques for analysis of gaseous constituents.

DISCLOSURE OF INVENTION

It is, therefore, an object of the present invention to provide a sample bag for collecting a mixture of gasses for analysis that is made of a modified polymer that limits the effects of diffusion through the bag walls and limits the effect of residual gasses within the bag walls on the integrity of the collected sample.

In carrying out the above object and other objects and features of the present invention, a sample bag for collecting a mixture of gasses for analysis is provided. The sample bag is made of a modified polymer consisting essentially of tetrafluoroethylene (TFE) and at most about 2.0 percent perfluoropropylvinylether (PPVE). The modified polymer is melt processable, unlike conventional polytetrafluoroethylene (PTFE). Because the modified polymer may be heat sealed and bonded to itself by various welding techniques, the modified polymer reduces the effects of diffusion through the sample bag walls and residual gasses in the sample bag walls.

The amount of perfluoropropylvinylether (PPVE) co-monomer in the modified polymer may vary depending on the desired properties for the sample bag. That is, the modified polymer for the sample bag consists essentially of tetrafluoroethylene (TFE) and at most about 2.0 percent perfluoropropylvinylether (PPVE), and preferably, at most about 1.5 percent perfluoropropylvinylether (PPVE). More preferably, the modified polymer includes at most about 1.0 percent perfluoropropylvinylether (PPVE) co-monomer. More preferably, the modified polymer includes at most about 0.3 percent perfluoropropylvinylether (PPVE). More preferably, the modified polymer includes at most about 0.2 percent perfluoropropylvinylether (PPVE) co-monomer. More preferably, the modified polymer includes at least about 0.05 percent perfluoropropylvinylether (PPVE) co-monomer. In a suitable application, the modified polymer includes about 0.1 percent perfluoropropylvinylether (PPVE). It is appreciated that the percentages are mass percentages, as is readily understood by one skilled in the polymer arts.

Further, in carrying out the present invention, a method of collecting a diluted exhaust gas mixture from an internal combustion engine is provided. The method comprises receiving an exhaust gas mixture, receiving a dilution gas, mixing the dilution gas with the exhaust gas mixture to form the diluted exhaust gas mixture, and collecting the diluted gas exhaust gas mixture in a sample bag. The sample bag is made of a modified polymer consisting essentially of tetrafluoroethylene (TFE) and at most about 2.0 percent perfluoropropylvinylether (PPVE). It is appreciated that the amount of perfluoropropylvinylether (PPVE) co-monomer in the modified polymer may vary depending on the particular desired properties for the sample bag.

Still further, in carrying out the present invention, a sample bag for collecting diluted exhaust gasses from an internal combustion engine is provided. The sample bag comprises a boundary structure and an inlet connected to the structure for receiving the gasses. The boundary structure defines a container for the gasses. The structure is made of a modified polymer consisting essentially of tetrafluoroethylene (TFE) and at most about 2.0 percent perfluoropropylvinylether (PPVE). It is appreciated that the amount of perfluoropropylvinylether (PPVE) co-monomer may vary depending on the particular application and properties desired for the sample bag.

The advantages associated with embodiments of the present invention are numerous. For example, a sample bag for collecting a mixture of gasses for analysis that is made of the modified polymer consisting essentially of tetrafluoroethylene (TFE) and at most about 2.0 percent perfluoropropylvinylether (PPVE) reduces the effects of diffusion through the bag walls and the effects of residual gasses in the bag walls (emission and absorption by the walls) on the integrity of the sample. That is, a sample bag made of the modified polymer overcomes limitations associated with other sample bags including sample bags made of pure polytetrafluoroethylene (PTFE).

The above object and other objects, features, and advantages of the present invention are readily apparent from the following detailed description of the best mode for carrying out the invention when taken in connection with the accompanying drawings.

BEST MODE FOR CARRYING OUT THE INVENTION

Figure 1:
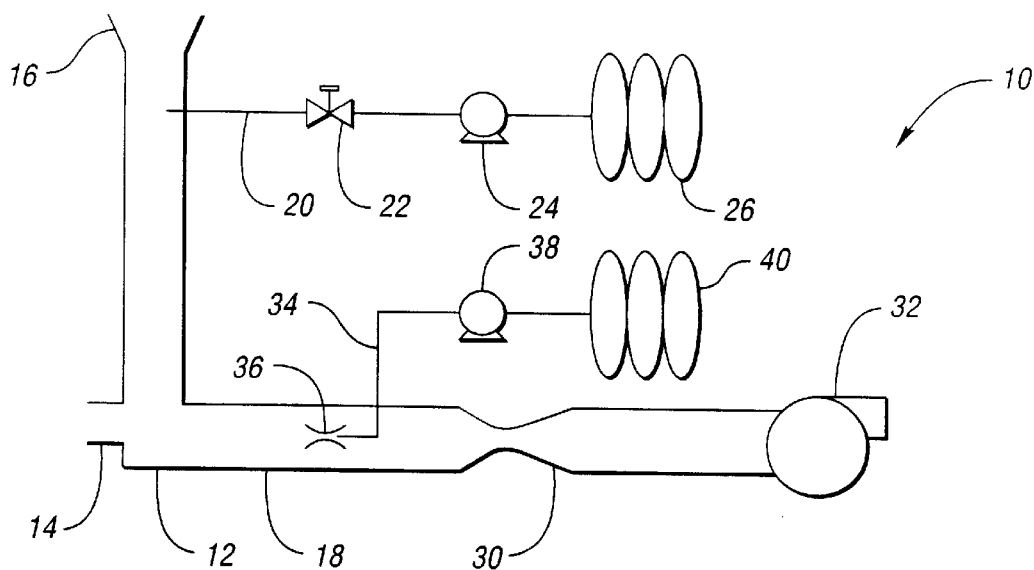
FIG. 1 is a schematic diagram illustrating a CVS connected to sample bags of the present invention.

Referring to FIG. 1, a CVS is generally indicated at 10. CVS 10 has a mixing portion 12, a gaseous inlet 14, a dilution inlet 16, and a mixture outlet 18. A dilution sample line 20, a needle valve 22 and a pump 24 cooperate to fill sample bags 26 with dilution gas.

Raw exhaust from the vehicle under test enters gaseous inlet 14 and is mixed with dilution air. The mixed gasses are drawn through a main venturi 30 by a blower 32. Main venturi 30 is sonic, or choked, and meters and measures the flow of the combined gasses. A mixture sample line 34 connects to mixture outlet 18 through a smaller, sample venturi 36 also operated in sonic or choked condition. A pump 38 cooperates with sample venturi 36 to fill sample bags 40 with the mixed gasses for later analysis.

Of course, it is appreciated that the sample bag of the present invention may be used in any suitable mixture collecting apparatus and is not limited to the specific CVS illustrated in FIG. 1. In accordance with the present invention, the sample bags 26 and 40 are made of a modified polymer consisting essentially of tetrafluoroethylene (TFE) and at most about 2.0 percent perfluoropropylvinylether (PPVE). The modified polymer of TFE with a small amount of PPVE co-monomer has improved performance over a sample bag made of pure PTFE. Specifically, while developing the present invention, PTFE film had been tested as material for the sample bag walls, and heated methods were used for fabrication which sealed the walls together. PTFE possesses some of the desired qualities for a sample bag but has high permeability to some gasses of interest due to its method of manufacture. Specifically, the PTFE sample bags have high permeability to diluted exhaust gas mixtures that are collected in automotive sampling systems.

Although PTFE sample bags have been used successfully because most forms of PTFE do not have a plastic or fluid phase, very small voids exist in the fabricated materials which allows gasses to be trapped within the material, and also allow the diffusion of gasses through the walls of the thin film itself. That is, when the sample bags are made of pure PTFE, diffusion through the sample bag walls reduces the integrity of the sample, and the bag walls may emit and absorb gasses, compromising the integrity of the present sample as well as future samples in the same sample bag. In accordance with the present invention, a modified polymer of PTFE with TFE and PPVE as co-monomers is used to make a sample bag. The improved material, unlike pure PTFE, may be melt processed, to fill the voids in the base product. The resulting modified polymer material has significantly reduced permeability to the gasses of interest and has reduced the presence of voids, so that the emission and absorption of gasses by the bag walls themselves is reduced. A suitable material for a sample bag of the present invention is known as TFM™ PTFE, and is available from Dyneon LLC, Oakdale, Minn.

Figure 2:
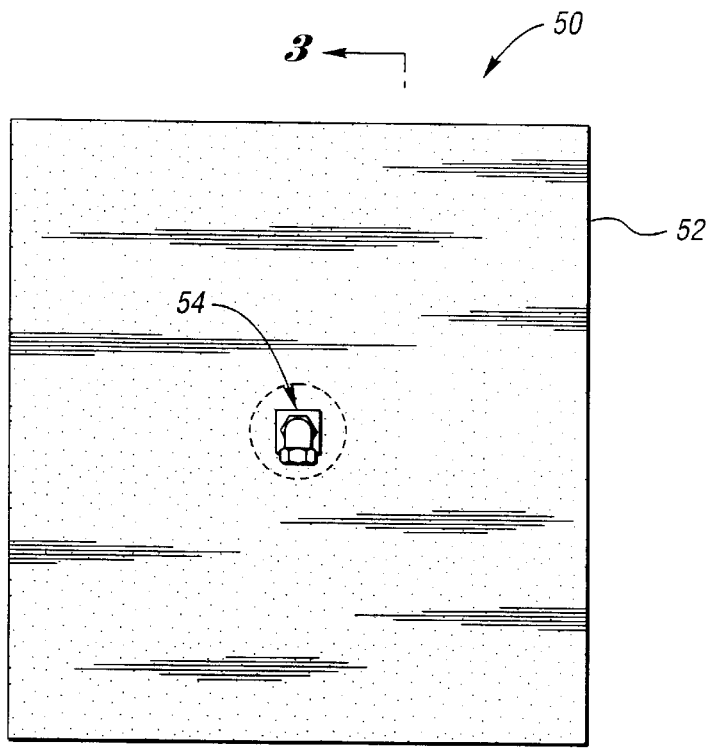
FIG. 2 is a front view of a sample bag of the present invention.
Figure 3:
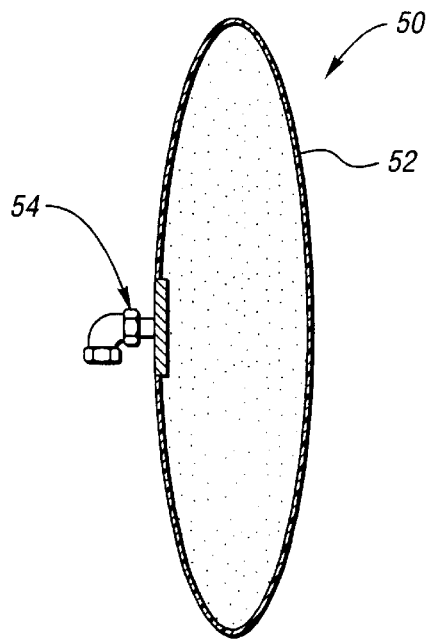
FIG. 3 is a cross-sectional view taken along line 3—3 of FIG. 2.

As shown in FIGS. 2 and 3, a sample bag 50 includes a boundary structure 52 forming the sample bag walls. The boundary structure defines a container for the gasses and is made of a modified polymer consisting essentially of tetrafluoroethylene (TFE) and at most about 2.0 percent perfluoropropylvinylether (PPVE). Of course, the amount of PPVE may vary depending on the particular properties desired for the bag. It is to be appreciated that the small amount of PPVE co-monomer dramatically improves the properties of the sample bag walls. For example, the sample bag walls made of the modified polymer have improved weldability, lower permeability, and other improved properties. At the same time, the modified polymer still has many of the desirable properties of pure PTFE such as chemical resistance and thermal stability. For sample bags of the present invention, it is appreciated that the denser polymer structure with lower permeability and fewer voids is very advantageous to reduce the effects of diffusion of gasses through the walls, and the emission and absorption of gasses into and out of the bag walls, in turn, providing an overall higher integrity of the gas sample collected in the bag than existing sample bags including pure PTFE sample bags.

Figure 4:
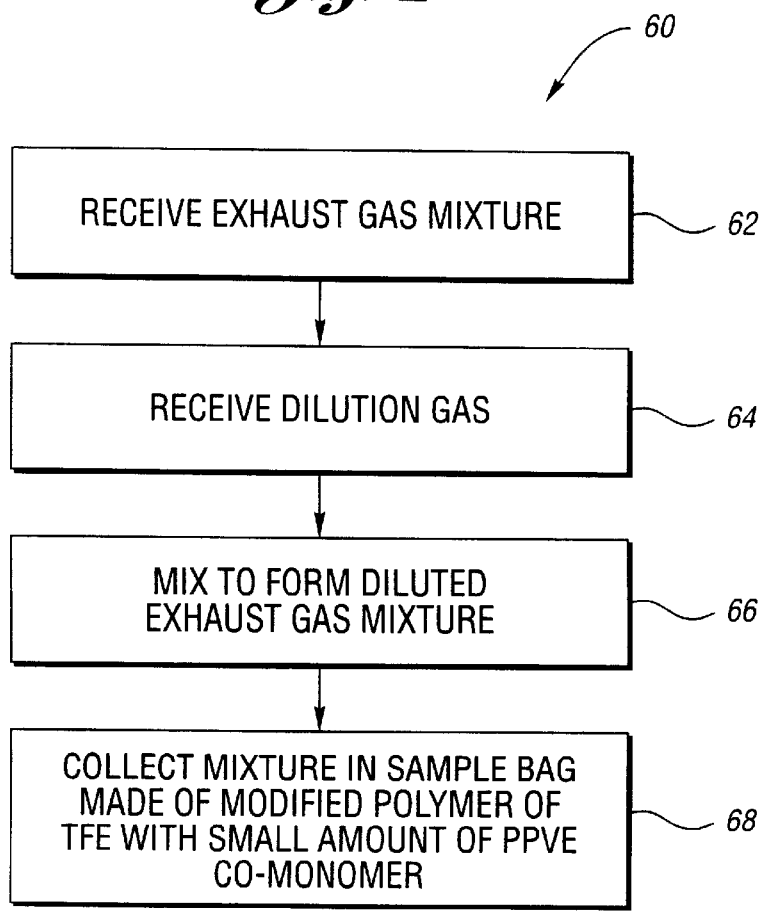
FIG. 4 is a block diagram illustrating a method of the present invention for collecting a mixture in a sample bag made of a modified polymer of TFE with a small amount of PPVE co-monomer.

In FIG. 4, a method of the present invention is generally indicated at 60. At block 62, an exhaust gas mixture is received. At block 64, a dilution gas is received. At block 66, the dilution gas and the exhaust gas mixture are mixed to form a diluted gas mixture. At block 68, a diluted exhaust gas mixture is collected in the sample bag. The sample bag, in accordance with the present invention, is made of a modified polymer of TFE with a small amount of PPVE co-monomer.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A sample bag for collecting diluted exhaust gases from an internal combustion engine, the sample bag comprising:

a boundary structure defining a container for the gases, the structure being made of a modified polymer consisting essentially of tetrafluoroethylene and at most about 2.0% perfluoropropylvinylether; and an inlet connected to the structure for receiving the gases.

2. The sample bag of claim 1 wherein the modified polymer consists essentially of tetrafluoroethylene and at most about 1.5% perfluoropropylvinylether.

3. The sample bag of claim 2 wherein the modified polymer consists essentially of tetrafluoroethylene and at most about 1.0% perfluoropropylvinylether.

4. The sample bag of claim 3 wherein the modified polymer consists essentially of tetrafluoroethylene and at most about 0.3% perfluoropropylvinylether.

5. The sample bag of claim 4 wherein the modified polymer consists essentially of tetrafluoroethylene and at most about 0.2% perfluoropropylvinylether.

6. The sample bag of claim 5 wherein the modified polymer consists essentially of tetrafluoroethylene and at least about 0.05% perfluoropropylvinylether.

7. The sample bag of claim 6 wherein the modified polymer consists essentially of tetrafluoroethylene and about 0.1% perfluoropropylvinylether.

* * * * *